US008089287B2

(12) United States Patent
Izadnegahdar

(10) Patent No.: US 8,089,287 B2
(45) Date of Patent: Jan. 3, 2012

(54) SOIL HUMIDITY EVALUATION WITH CONTACT FREE COUPLING

(76) Inventor: Alain Izadnegahdar, Orange Village, OH (US)

(*) Notice: Subject to any disclaimer, the term of this patent is extended or adjusted under 35 U.S.C. 154(b) by 1109 days.

(21) Appl. No.: 11/621,568

(22) Filed: Jan. 10, 2007

(65) Prior Publication Data

US 2010/0253369 A1  Oct. 7, 2010

(51) Int. Cl.
*G01R 27/26* (2006.01)
*G01R 27/08* (2006.01)
*G08B 21/00* (2006.01)
(52) U.S. Cl. .... 324/667; 324/663; 324/693; 340/870.16
(58) Field of Classification Search .................. 324/663, 324/667, 691–693; 340/870.16; 239/63
See application file for complete search history.

(56) References Cited

U.S. PATENT DOCUMENTS

| | | | | |
|---|---|---|---|---|
| 3,581,197 A | * | 5/1971 | Morey et al. | 324/690 |
| 3,771,548 A | * | 11/1973 | Rauchwerger | 137/392 |
| 5,445,178 A | * | 8/1995 | Feuer | 137/1 |
| 6,975,245 B1 | * | 12/2005 | Slater et al. | 340/870.16 |

* cited by examiner

*Primary Examiner* — Melissa Koval
*Assistant Examiner* — Farhana Hoque

(57) ABSTRACT

Systems and methods that evaluate moisture content of the soil through change of capacitance and alternative current. A contact free inductive coupling can be provided between a sensor arrangement associated with the soil, and a reader arrangement (e.g., combination of inductor(s) and capacitor(s)) to determine frequency changes of resulting sinusoidal oscillator. Such frequency change can be correlated with moisture content of the soil.

17 Claims, 7 Drawing Sheets

Parallel-interdigital capacitive sensor | Interdigital Capacitive Sensor in single Octogonal shape | Interdigital Capacitive Sensor in multi-circle Octogonal shape

SOIL HUMIDITY EVALUATION WITH CONTACT FREE COUPLING

BACKGROUND

Plants require sufficient amount of water in the host soil to assist in absorbing minerals, and stimulate adequate growth. In such environments, air helps formation of desired solutions of compounds and minerals, which are subsequently absorbed through the roots and carried to the leaves of the plant.

Both water deficiency and also excess amount of water can adversely affect such process, and hence the plant growth. For example, excess water being added to the soil is not able to properly drain away, and thus occupies minute air spaces between soil particles. Consequently, air is prevented from reaching minerals in the soil, and cannot adequately combine therewith to form necessary nutrients for the plants. If this condition persists, affected plant will die. Accordingly, maintaining a proper balance between air and water in the soil and suitable moisture content are critical factors for plant growth.

Control of soil moisture content can become challenging in closed environments such as households and green houses. The Moisture content of soil that hosts the plants needs to be maintained at an optimum level to prevent plant loss or retardation of growth. Electronic signaling devices that monitor moisture content often are negatively affected through electrolysis and rusting of conductive parts. For example, minerals from fertilizers can readily deposit on conductive parts that measure electrical resistance associated with adjacent soil, and hence provide inaccurate readings.

Likewise, commercially available non-electronic devices which operate by a chemical dye—(e.g., turning color from pink to blue in presence of moisture, or by a dark green piece of plastic turning a lighter green in absence of moisture) suffer from poor visibility, are highly inaccurate, and have a short operating lifetime. Because these chemical dye devices rely on capillary action that passively transports moisture from the soil to the sensing area of the device, they are subject to corrosion and precipitation of salts and fertilizer within the device, an operating parameter which effectively destroys accuracy and usability.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

The subject invention provides for systems and methods that evaluate moisture content of soil based on frequency changes of a sinusoidal oscillator, via employing a contact—free inductive coupling between a sensor arrangement and a reader arrangement (e.g., combination of inductor(s) and capacitor(s)) to determine the frequency changes of the sinusoidal oscillator.) Moreover, the sensor arrangement can further include a Printed Circuit Board (PCB) that includes electrically conductive lines, which in conjunction with surrounding soil medium can function as electrical capacitors. Such conductive lines can be suitably coated by electrically insulating material (e.g., polyurethane, epoxy, silicon nitride, silicon oxide, and the like) to mitigate electrolysis. Accordingly, AC signal can be employed for impedance measurement, and the conductive lines (e.g., electrodes) typically need not directly contact the soil.

According to a particular aspect of the subject innovation, the sensor arrangement includes a capacitive sensor(s) that contacts the soil (e.g., inserted within the soil) and/or is associated therewith (e.g., induces an electric field therein), and is operatively connected to a first coil, to form the sensor arrangement. Such first coil and capacitive sensor further function as an LC tank circuit (e.g., a passive circuit) that forms a first part of the sinusoidal oscillator. A second part of such sinusoidal oscillator is formed by the reader arrangement, wherein a second coil is part of such sinusoidal oscillator having a frequency that varies based on capacitance of the capacitive sensor. The sinusoidal oscillator can be powered up through a DC voltage source.

In accordance with a further aspect of the subject innovation, the sensor arrangement can further include a sinusoidal oscillator as part thereof. The capacitive sensor is operatively connected to the sinusoidal sensor, and the sinusoidal oscillator is powered through sensor coupling coils(s). A frequency employed for powering the sinusoidal oscillator (e.g., 100-300 KHz) is typically lower than the frequency of the output signal from such sinusoidal oscillator (e.g., 1 MHz-30 MHz). The output signal (e.g., frequency) of the sinusoidal oscillator is superposed on the signal that is employed for powering the sinusoidal oscillator. The reader arrangement can then isolate the output signal of the sinusoidal oscillator for further processing.

In a related methodology in accordance with an aspect of the subject innovation a capacitive sensor, (which induces an electric field within the soil) can sense a capacitance change resulting from a change of dielectric associated with the soil (e.g., loss/addition of moisture content affects soil dielectric.) Subsequently, such change of capacitance affects a resonant frequency of the sinusoidal oscillator. The resonant frequency of the sinusoidal oscillator can indicate a moisture content of the soil (e.g., predetermined calibration between resonant frequency and moisture content of soil.)

According to a further methodology in accordance with an aspect of the subject innovation, the sinusoidal oscillator behaves as a modulating load for the inductively coupled first and the second coil. Subsequently, such modulation can be detected by the reader arrangement. Such reader arrangement can further include a phased locked loop (PLL) circuit for reconstruction of the sinusoidal oscillator output signal—from the output signal of the sinusoidal oscillator that is superposed on the signal being employed for powering the sinusoidal oscillator. In a related aspect, the printed circuit boards comprise a plurality of conductive lines that induce an electric field within the soil medium. Such circuit board can include a planar coil and/or cylindrical coils (e.g., two cylindrical coaxial coils in spatial arrangement), which can be suitably coated. A moisture content of the soil affects a dielectric thereof, which in turn is sensed by the capacitive sensor.

The following description and the annexed drawings set forth in detail certain illustrative aspects of the claimed subject matter. These aspects are indicative, however, of but a few of the various ways in which the principles of such matter may be employed and the claimed subject matter is intended to include all such aspects and their equivalents. Other advantages and novel features will become apparent from the following detailed description when considered in conjunction with the drawings.

DETAILED DESCRIPTION

The various aspects of the subject innovation are now described with reference to the annexed drawings, wherein like numerals refer to like or corresponding elements throughout. It should be understood, however, that the drawings and detailed description relating thereto are not intended to limit the claimed subject matter to the particular form disclosed. Rather, the intention is to cover all modifications, equivalents and alternatives falling within the spirit and scope of the claimed subject matter.

Figure 1:
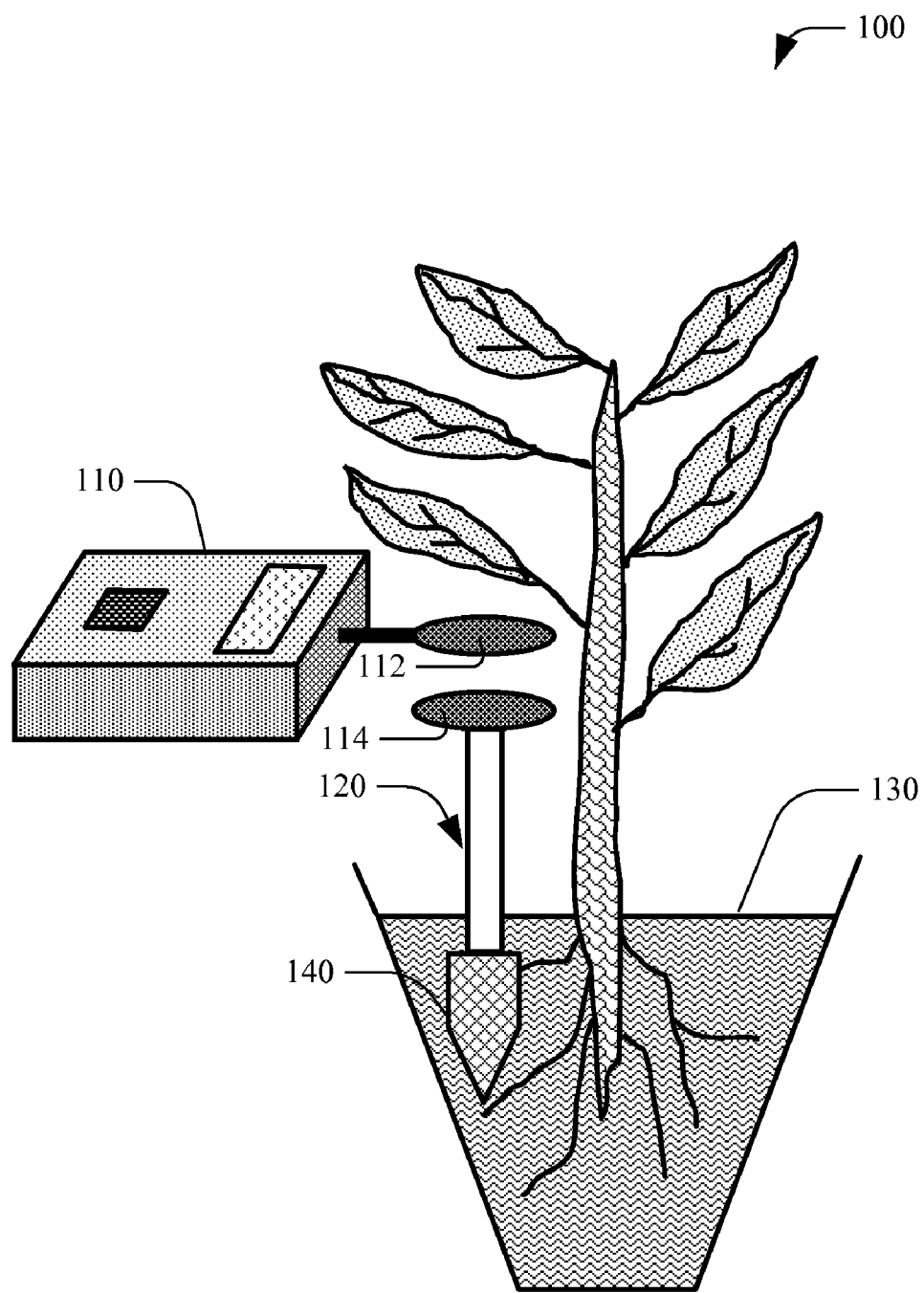
FIG. 1 illustrates a schematic diagram of an exemplary system that evaluates moisture content in accordance with an aspect of the subject innovation.

FIG. 1 illustrates a system 100 for evaluation of moisture content for soil in accordance with an aspect of the subject innovation. The system 100 includes a reader arrangement 110 that includes a first coil 112, and a sensor arrangement 120 that has a second coil 114, which interact via a contact-free inductive coupling for a read of moisture content for the soil 130. The reader arrangement 110 (e.g., the first coil 112) is brought into proximity (e.g., 0-1 cm apart) of the sensor arrangement 120 (e.g. in proximity of second coil 114). A printed circuit board 140 of the sensor arrangement can be inserted into the soil 130. The system 100 operates based on an electrical capacitive variance and change of dielectric associated with the soil (as opposed to conventional systems that typically operate based on electrical resistive variance). The printed circuit board 140 includes electrically conductive lines, which induce an electric field within surrounding soil medium and in conjunction therewith can function as electrical capacitor(s).

Figure 2:
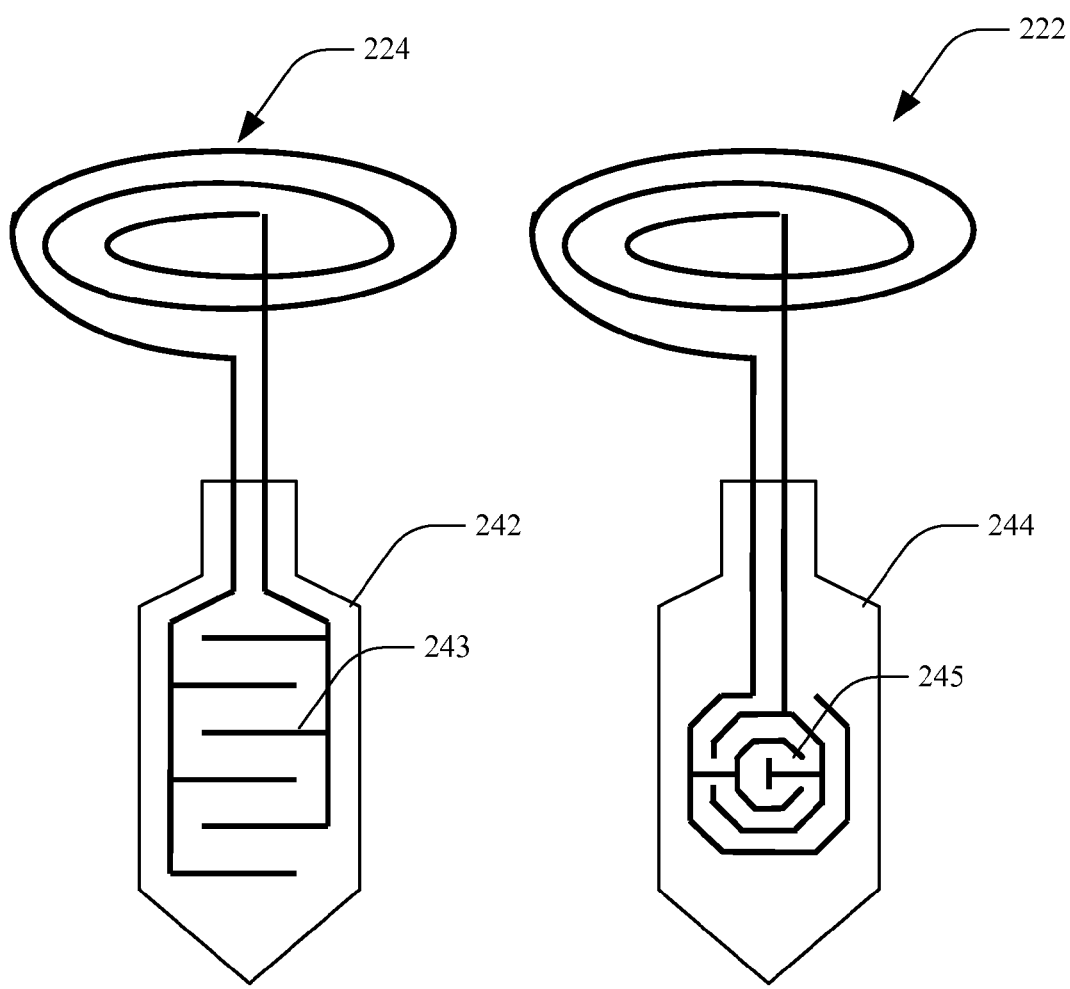
FIG. 2 illustrates a schematic diagram of a capacitive soil moisture sensor arrangement and associated reader arrangement in accordance with an aspect of the subject innovation.

FIG. 2 illustrates schematic diagram of exemplary sensor arrangements in accordance with an aspect of the subject innovation. Each of the sensor arrangements 222 or 224 can interact via a contact free inductive coupling with a reader arrangement (not shown), to supply readings for moisture content of the soil based on a change of dielectric of the soil. Moreover, each of the sensor arrangements 222, 224 can include a respective printed circuit board 242, 244 that induces an electric contacts the soil (e.g., inserted therein.) Such printed circuit board 242, 244 can include a plurality of conductive trace configurations such as linear form 243, multi-lateral polygon shaped 245, circular, co-centric, arcs, and combinations thereof. A conductive trace(s) in conjunction with surrounding soil medium can function as electrical capacitors, wherein a change of moisture of the soils affects a dielectric thereof, and hence results in a change in capacitance of the electrical capacitors. Furthermore, the conductive lines/shapes 243, 245 can be suitably coated by electrically insulating material (e.g., polyurethane, epoxy, silicon nitride, silicon oxide, and the like) to mitigate or eliminate electrolysis.

Figure 3:
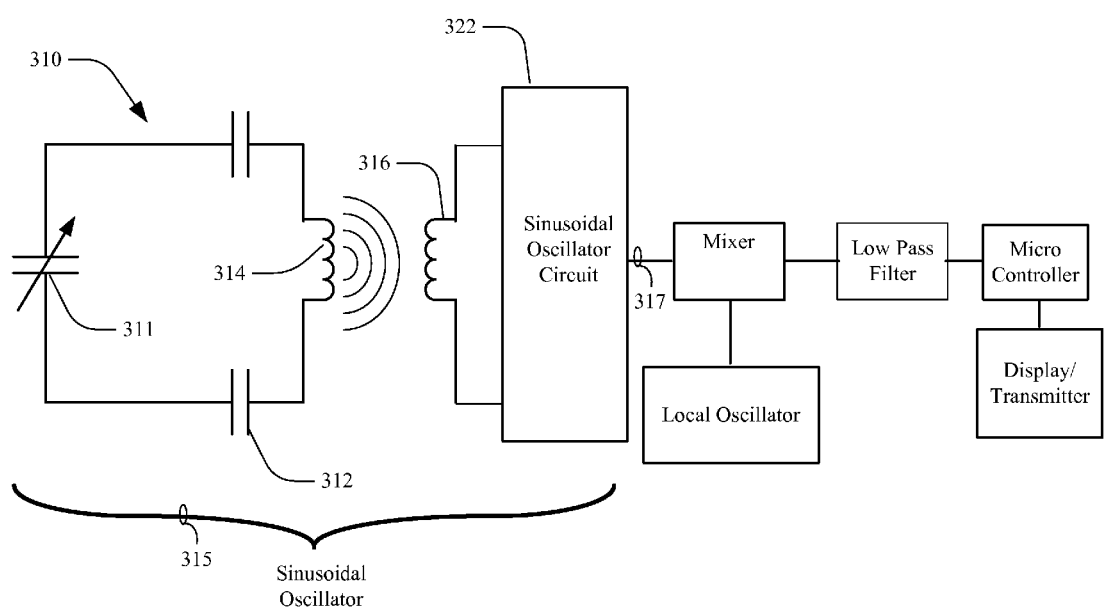
FIG. 3 illustrates a circuit block diagram for a sensor arrangement and a reader arrangement in accordance with an aspect of the subject innovation.

FIG. 3 illustrates a block diagram for interaction between a sensor arrangement and a reader arrangement according to a particular aspect of the subject innovation. A capacitive sensor 312 is connected to a first coil 314 to form the sensor arrangement 310. When the first coil 314 is brought into substantial close proximity (e.g., 0-10 mm) of the second coil 316, the frequency of the sinusoidal oscillator circuit 322 is reduced.

The sinusoidal oscillator circuit 322 is connected to a second coil 316 and in combination with the sensor arrangement 310 form the sinusoidal oscillator 315. When the sinusoidal oscillator circuit 322 is powered up and the capacitive sensor 312 senses a capacitance variance that is associated with dieelectric changes of the soil (e.g., from moisture change) 311, then the frequency of the sinusoidal oscillator circuit 322 can change based on the capacitance variance as determined by the capacitive sensor 312. Such frequency change of the sinusoidal oscillator 315 can be measured and employed as an index for evaluating change of moisture within the soil 311, which is in contact with the capacitive sensor 312 (e.g., a change of soil moisture content affects soil dielectric, which ultimately changes a measured capacitance of a region associated with capacitive sensor—such as for example a region of soil adjacent to the capacitive sensor, wherein electrical fields are induced therein.) Hence, a frequency of the sinusoidal oscillator 315 also changes. Such changes can then be calibrated to correspond with changes of the moisture content of the soil 311 that receives an electric field from, and/or is in contact with the capacitive sensor 312. As illustrated in FIG. 3, the sinusoidal oscillator 315 can includes: the sensor arrangement 310, the sinusoidal oscillator circuit 322, and the second coil 316. It is to be appreciated that the output signal 317 is the same for the sinusoidal oscillator 315 and the sinusoidal oscillator circuit 322. Moreover, it is to be appreciated that FIG. 3 is an exemplary block diagram of a passive circuit as part of the sensor arrangement 310, and other arrangements with active components (e.g., transistors, diodes, and the like) are well within the realm of the subject innovation.

Figure 4:
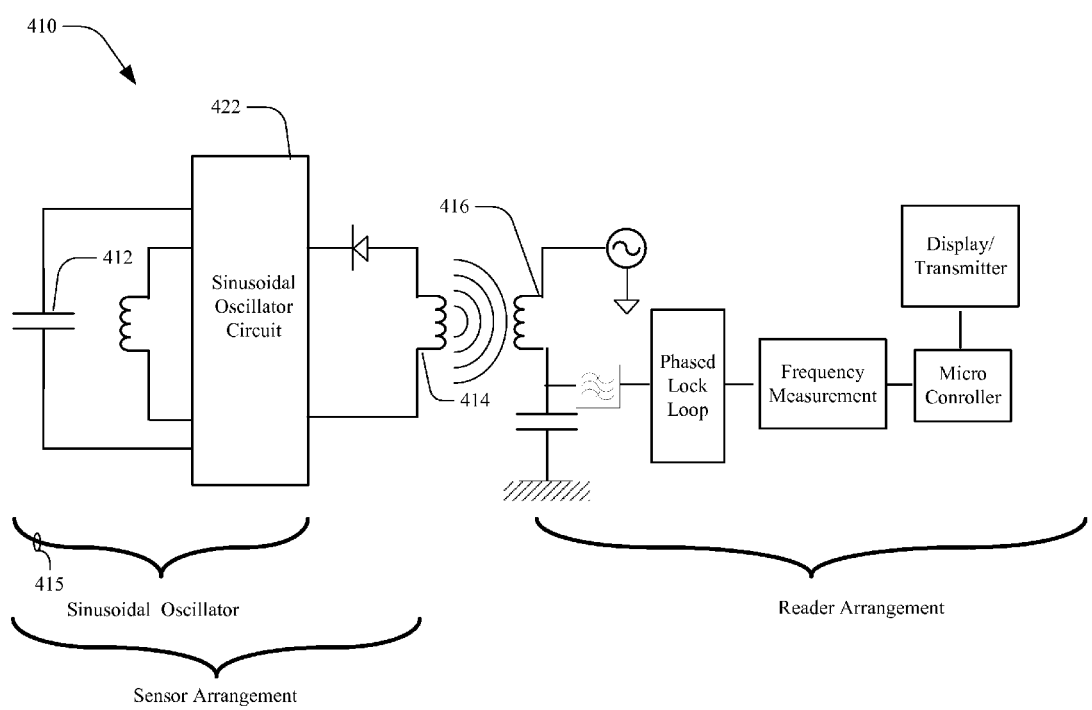
FIG. 4 illustrates a further circuit block diagram for a further sensor and reader arrangement in accordance with an aspect of the subject innovation.

For example, FIG. 4 illustrates another block diagram wherein the sinusoidal oscillator circuit 422 becomes part of the sensor arrangement 410. The capacitive sensor 412 is operatively connected to the sinusoidal oscillator circuit 422, wherein the sinusoidal oscillator circuit 422 is powered through sensor coupling coils(s) 414, 416. A frequency employed for powering the sinusoidal oscillator circuit 422 (e.g., 100-300 KHz) is typically lower than the frequency of the output signal from such sinusoidal oscillator (e.g., 1 MHz-30 MHz). The output signal (e.g., frequency) of the sinusoidal oscillator 415 is superposed on the signal that is employed for powering the sinusoidal oscillator circuit 422. The reader arrangement can then isolate the output signal of the sinusoidal oscillator for further processing.

Figure 5:
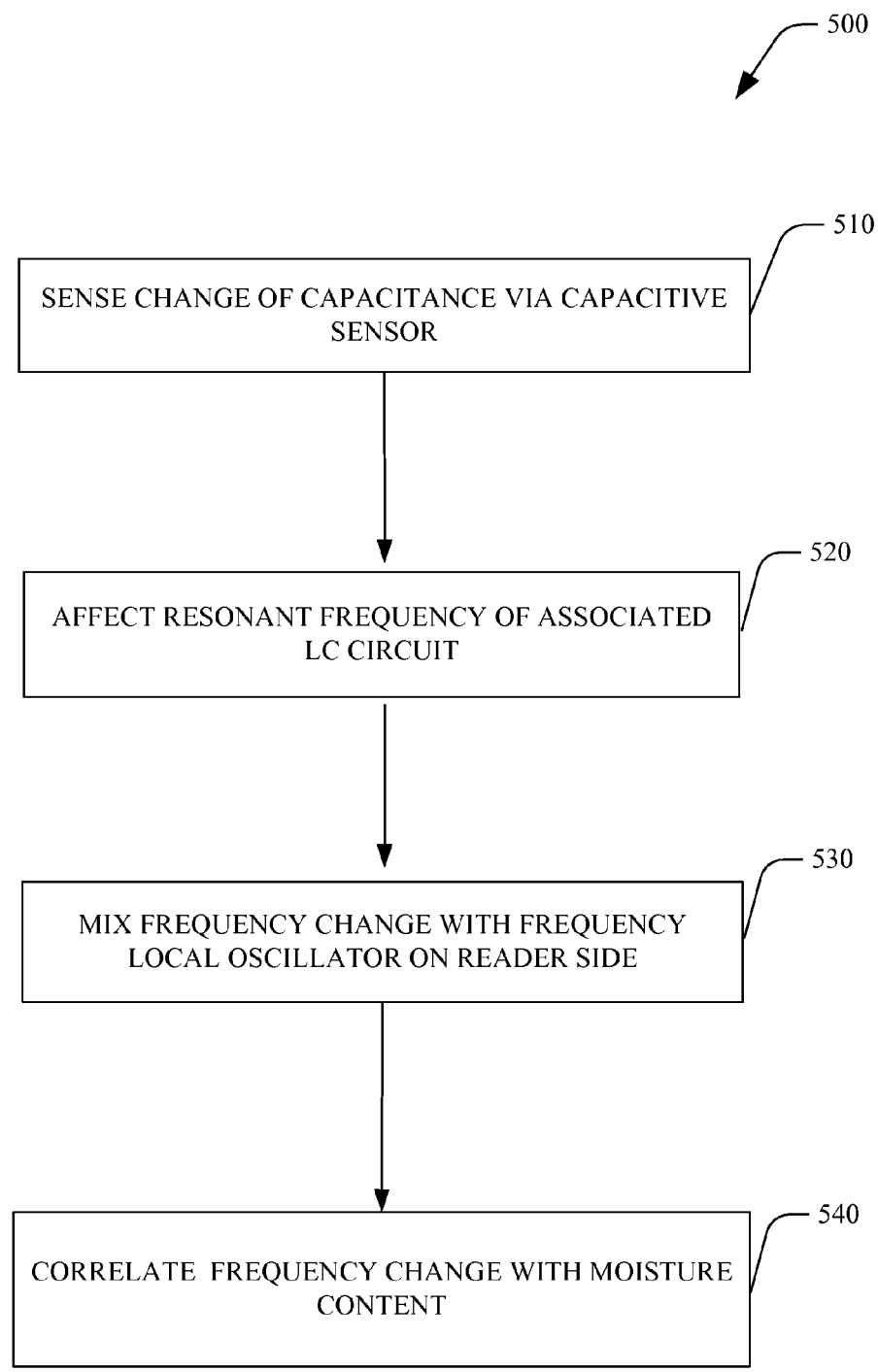
FIG. 5 illustrates a particular methodology for evaluation of soil moisture content in accordance with an aspect of the subject innovation.

FIG. 5 illustrates a related methodology 500 in accordance with an aspect of the subject innovation. While the exemplary method is illustrated and described herein as a series of blocks representative of various events and/or acts, the subject innovation is not limited by the illustrated ordering of such blocks. For instance, some acts or events may occur in different orders and/or concurrently with other acts or events, apart from the ordering illustrated herein, in accordance with the innovation. In addition, not all illustrated blocks, events or acts, may be required to implement a methodology in accordance with the subject innovation. Moreover, it will be appreciated that the exemplary method and other methods according to the innovation may be implemented in association with the method illustrated and described herein, as well as in association with other systems and apparatus not illustrated or described. Initially, and at 510 a capacitive sensor, (which is in contact with the soil, and/or induces an electric field therein) can sense a capacitance change resulting from a change of dielectric associated with the soil (e.g., loss/addition of moisture content associated therewith.) Subsequently, and at 520 such change of capacitance affects a resonant frequency of an associated LC circuit. Next and at 530, the frequency change can then be mixed with frequency of a local oscillator on the reader side, wherein the measured frequency is subtracted from the frequency of a local oscillator. Such difference can then be linearized and/or calibrated in accordance with an aspect of the subject innovation at 540, to correlate with moisture content of the soil.

Figure 6:
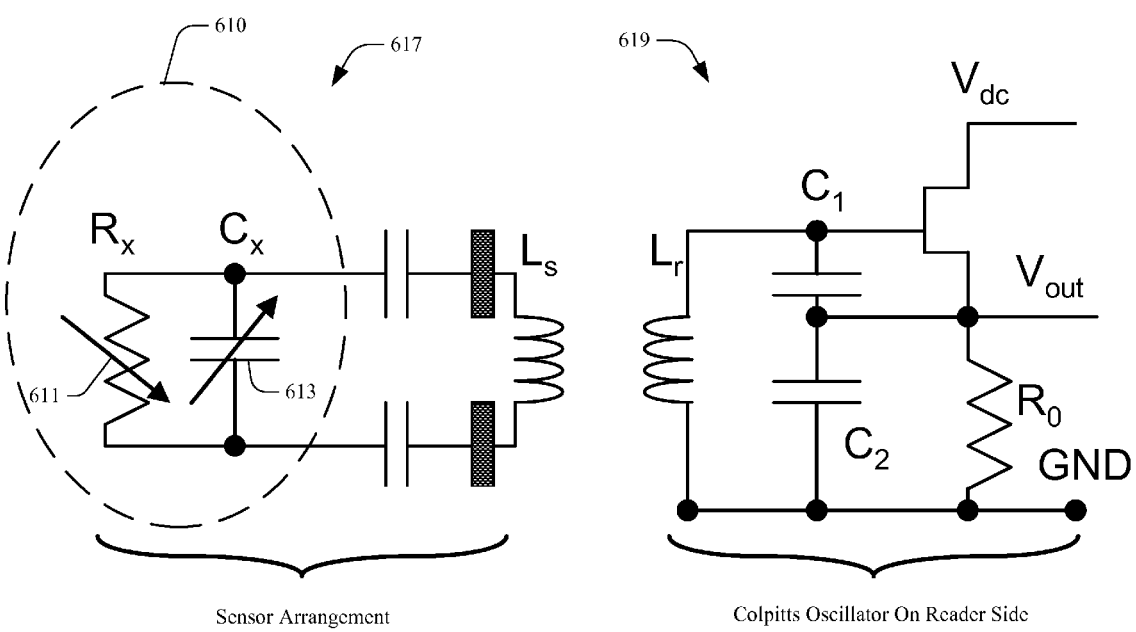
FIG. 6 illustrates an exemplary electrical circuit that is equivalent to an arrangement in accordance with an aspect of the subject innovation.

FIG. 6 illustrates an exemplary electrical circuit that is equivalent to an arrangement in accordance with an aspect of the subject innovation. A printed circuit board associated with the reader arrangement can induce an electric field within adjacent soil. Conductive traces on such printed circuit board can act as electrodes to induce an electric field within the adjacent soil. The electrical impedance of soil measured between and/or adjacent to the electrodes has a resistive component (Rx) 611 and a capacitive 613 component ($C_x$), as part of an electrical circuit model 610. The capacitive component 613 can occur due to moisture content and a substantially high dielectric constant of water ($\in_r$=78 to 81), which can exist in the soil. The resistive component 611 can exist due to dissolved minerals in the water absorbed by the soil. Percentage of water present in the soil causes variation of capacitance, which is employed by systems in accordance with the subject innovation.

Even though both resistive and capacitive components of the soil impedance vary based on moisture content of the soil, the subject innovation mitigates problems with conventional systems that employ electrical resistance measurement (e.g., conventional systems employ direct current voltage that can cause chemical reaction and electrolysis that lead to corrosion of electrodes.)

As explained earlier, one aspect of the subject innovation employs an LC resonance circuit (e.g., a capacitor and a first coil) that changes resonance frequency according to a capacitor value that employs alternative current. As illustrated in FIG. 6, the LC circuit 617 couples to an LC oscillator 619 (e.g., colpits oscillator) that is located on the reader side, wherein value of $C_x$ can affect the frequency of the oscillator, and yet the value of Rx will typically not have effect on the frequency of oscillation.

As explained in detail supra, a change in capacitance of the sensor arrangement can change frequency of the oscillator (e.g., a change of about 5% to 10% in frequency.) Such an LC circuit 617 of the subject innovation can in general mitigate effects of resistance (e.g., resulting from resistive component 611) associated with conventional devices that employ RC oscillators. Moreover, by employing an LC circuit 617 in accordance with an aspect of the subject innovation DC bias across plates of the capacitor can typically be eliminated.

It is to be appreciated that illustrated circuits described herein are exemplary in nature, and other circuits are well within the realm of the subject innovation. For example, an extra capacitor can be added in series in the sensor LC circuit to limit the maximum value of capacitance change and/or a predetermined value for capacitance, wherein $$C_{equivalent}=(C_{sensor}*C_{limit})/(C_{sensor}+C_{limit})$$

Figure 7:
FIG. 7 illustrates exemplary printed circuit boards that have planar configurations in accordance with an aspect of the subject innovation.
Figure 7:
Figure 7:

FIG. 7 illustrates an exemplary printed circuit board that has a planar configuration 700 of conductive traces 710 in accordance with an aspect of the subject innovation. Such conductive traces that form plates/electrodes for capacitive sensor induce electric fields within adjacent soil and can be suitably coated by electrically insulating material (e.g., polyurethane, epoxy, silicon nitride, silicon oxide, and the like) to mitigate or eliminate electrolysis. It is to be appreciated that non-planar circuit boards (e.g., spatial coaxial cylinders) can also be employed for inducing electric fields within the soil and/or functioning as plates/electrodes for the capacitive sensors.

The word "exemplary" is used herein to mean serving as an example, instance or illustration. Any aspect or design described herein as "exemplary" is not necessarily to be construed as preferred or advantageous over other aspects or designs. Similarly, examples are provided herein solely for purposes of clarity and understanding and are not meant to limit the subject innovation or portion thereof in any manner. It is to be appreciated that a myriad of additional or alternate examples could have been presented, but have been omitted for purposes of brevity.

Furthermore, all or portions of the subject innovation can be implemented as a system, method, apparatus, or article of manufacture using standard engineering techniques to produce software, circuits to implement the disclosed innovation.

What has been described above includes various exemplary aspects. It is, of course, not possible to describe every conceivable combination of components or methodologies for purposes of describing these aspects, but one of ordinary skill in the art may recognize that many further combinations and permutations are possible. Accordingly, the aspects described herein are intended to embrace all such alterations, modifications and variations that fall within the spirit and scope of the appended claims.

Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A soil moisture content indicator comprising:
   a sensor arrangement that senses an electrical capacity change of a capacitive sensor, the capacitive sensor induces an electric field into a soil medium associated therewith, and
   a reader arrangement that is operatively connected to the sensor arrangement via a contact free inductive coupling,
   a sinusoidal oscillator that includes a first part and a second part, the first part is formed by the capacitive sensor; the second part is formed by the reader arrangement,
   wherein, a structure of the sinusoidal oscillator is creatable by the contact free inductive coupling of the reader arrangement and the sensor arrangement; and
   a frequency of the sinusoidal oscillator varies based on the electrical capacity change of the capacitive sensor, to reflect moisture content of the soil medium.

2. The soil moisture content indicator of claim 1, the capacitive sensor formed via conductive traces on a printed circuit board associated with the sensor arrangement.

3. The soil moisture content indicator of claim 2, the conductive traces coated by electrically insulating material.

4. The soil moisture content indicator of claim 3, the sensor arrangement further includes a first coil that is operatively connected to the capacitive sensor.

5. The soil moisture content indicator of claim 4, the reader arrangement with a second coil that interacts with the first coil to create inductive coupling.

6. The soil moisture content indicator of claim 2, the printed circuit board with a planar configuration or cylindrical coils in spatial arrangement.

7. The soil moisture content indicator of claim 1, the sinusoidal oscillator includes a sinusoidal circuit that is part of the reader arrangement.

8. The soil moisture content indicator of claim 7, the sinusoidal oscillator circuit is a Colpits oscillator.

9. The soil moisture content indicator of claim 1, the sinusoidal oscillator includes a sinusoidal circuit that is part of the sensor arrangement.

10. A method of evaluating soil moisture content comprising:
sensing a change of soil dielectric via a capacitive sensor that induces an electric field within soil; the capacitive sensor part of a passive sensor arrangement of a soil moisture content indicator;
changing a frequency of a sinusoidal oscillator based on the change of soil dielectric,
inductively coupling the sensor arrangement and a reader arrangement to form part of the sinusoidal oscillator, and
superposing an output signal of the sinusoidal oscillator on top of a signal for powering the sinusoidal oscillator, a frequency of the output signal for the sinusoidal oscillator is higher than frequency of the signal for powering the sinusoidal oscillator.

11. The method of claim 10 further comprising coupling an LC circuit on the sensor arrangement with an LC oscillator on the reader arrangement.

12. The method of claim 11 further comprising eliminating DC bias on plates of the capacitive sensor.

13. The method of claim 10 further comprising inducing an electric field in the soil via a printed circuit board.

14. The method of claim 10 further comprising limiting a value of capacitance change associated with changes of the soil dielectric.

15. The method of claim 10 further comprising supplying power to a sinusoidal oscillator circuit of the sensor arrangement via inductive coupling from the reader arrangement.

16. The method of claim 15 further comprising superposing an output signal of the sinusoidal oscillator with signal employed for powering a sinusoidal circuit that is part of the sensor arrangement.

17. The method of claim 16 further comprising isolating the output signal of the sinusoidal oscillator by the reader arrangement.

\* \* \* \* \*